(12) United States Patent
Sauer (10) Patent No.: US 11,826,036 B2
(45) Date of Patent: Nov. 28, 2023

(54) EPIGASTRIC RETRACTOR

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 18/073,801

(22) Filed: Dec. 2, 2022

(65) Prior Publication Data

US 2023/0172601 A1 Jun. 8, 2023

Related U.S. Application Data

(60) Provisional application No. 63/285,515, filed on Dec. 3, 2021.

(51) Int. Cl.
*A61B 17/02* (2006.01)

(52) U.S. Cl.
CPC .................. *A61B 17/0281* (2013.01)

(58) Field of Classification Search
CPC . A61B 17/02; A61B 17/0281; A61B 17/0206; A61B 2017/0262; A61B 1/32
USPC ........................................................ 600/235
See application file for complete search history.

(56) References Cited

U.S. PATENT DOCUMENTS

| | | |
|---|---|---|
| 1,944,009 A | 1/1934 | Homer |
| 3,882,855 A | 5/1975 | Schulte et al. |
| 4,048,987 A | 9/1977 | Hurson |
| 5,865,731 A | 2/1999 | Lenox et al. |
| 5,908,382 A | 6/1999 | Koros et al. |
| 6,159,231 A | 12/2000 | Looney et al. |
| 6,228,024 B1 | 5/2001 | Co et al. |
| 6,241,658 B1 | 6/2001 | Goodrich |
| 6,340,345 B1 * | 1/2002 | Lees .................. A61B 17/0206 600/226 |
| 6,692,434 B2 | 2/2004 | Ritland |
| 6,855,149 B2 | 2/2005 | Dye |
| 6,951,538 B2 | 10/2005 | Ritland |
| 7,311,662 B2 | 12/2007 | Holland et al. |
| 7,389,710 B2 | 6/2008 | Phillips et al. |
| 7,396,328 B2 | 7/2008 | Penenberg |
| 7,871,374 B2 | 1/2011 | De Canniere et al. |

(Continued)

FOREIGN PATENT DOCUMENTS

| | | |
|---|---|---|
| CN | 20199698 | 10/2011 |
| FR | 1235135 | 10/1960 |
| WO | 2007/075882 | 7/2007 |

*Primary Examiner* — Eduardo C Robert
*Assistant Examiner* — Christina Negrellirodriguez
(74) *Attorney, Agent, or Firm* — Michael E. Coyne (57) ABSTRACT

A retractor member includes a body portion extending along a longitudinal axis and being at least partially defined by a first lateral perimeter edge and a second lateral perimeter edge that each extends parallel to the longitudinal axis. The body portion additionally includes an upper surface and a lower surface that each extends between the first lateral perimeter edge and the second lateral perimeter edge. A first lateral support portion is coupled to the body portion at a first location at or adjacent to the first lateral perimeter edge, and a second lateral support portion is coupled to the body portion at a second location at or adjacent to the second lateral perimeter edge. A first coupling portion is disposed at a top end portion of the first lateral support portion and a second coupling portion is disposed at a top end portion of the second lateral support portion.

20 Claims, 9 Drawing Sheets

(56) References Cited

U.S. PATENT DOCUMENTS

| | | |
|---|---|---|
| 8,197,405 B2 | 6/2012 | Lindsay et al. |
| 9,918,708 B2 | 3/2018 | Livne et al. |
| 10,973,547 B1 | 4/2021 | Buerchner et al. |
| 2004/0242970 A1 | 12/2004 | Burns |
| 2005/0192484 A1* | 9/2005 | Sharratt ............. A61B 17/0293 600/210 |
| 2007/0066872 A1* | 3/2007 | Morrison ............... A61B 17/02 600/245 |
| 2012/0296172 A1* | 11/2012 | Raven, III ......... A61B 17/0206 600/231 |

* cited by examiner

EPIGASTRIC RETRACTOR

CROSS-REFERENCE TO RELATED APPLICATIONS

This application claims the benefit of U.S. Provisional Patent Application No. 63/285,515, filed Dec. 3, 2021, which is incorporated by reference herein in its entirety.

FIELD OF THE INVENTION

The claimed invention relates to surgical devices, and more specifically to a retractor.

BACKGROUND OF THE INVENTION

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right ITA, or the left or right internal mammary artery (IMA) may utilize access to the ITAs via sub-xiphoid access, where increased surgical space is gained by accessing the internal thoracic arteries via incision at the subxiphocostal region.

While less invasive surgical approaches for ITA harvesting and CABG have shown promise, visualization, maintenance of insufflation, and distal suturing of a coronary anastomosis in totally endoscopic coronary artery bypass grafting on the beating heart is technically demanding. Moreover, with obese patients, subcutaneous fat in the epigastric region may obstruct access to the incision and the subxiphocostal region. Thus, there is a need for larger working spaces to accommodate an increased range of motion during surgical procedures, as well as room for additional surgical tools, such as endoscopes, suturing tools, and the like.

BRIEF SUMMARY OF THE INVENTION

A retractor member includes a body portion extending along a longitudinal axis from a proximal end to a distal end. The body portion is at least partially defined by a first lateral perimeter edge that extends generally parallel to the longitudinal axis and a second lateral perimeter edge that extends generally parallel to the longitudinal axis. The body portion is also at least partially defined by an upper surface that extends between the first lateral perimeter edge and the second lateral perimeter edge and a lower surface that extends between the first lateral perimeter edge and the second lateral perimeter edge. The retractor member further includes a first lateral support portion coupled to the body portion at a first location at or adjacent to the first lateral perimeter edge, a second lateral support portion coupled to the body portion at a second location at or adjacent to the second lateral perimeter edge, a first coupling portion disposed at a top end portion of the first lateral support portion, and a second coupling portion disposed at a top end portion of the second lateral support portion. One of the first coupling portion or the second coupling portion is configured to be removably and rotatably secured to a coupling portion disposed at a distal end of a surgical support instrument that is adapted to stabilize and support the retractor member, and wherein the retractor member is configured to be selectively repositionable relative to the coupling portion at the distal end of a surgical support instrument such that the lower surface of the body portion is configured to be disposed in contact with a portion of a patient's tissue that is adjacent to a sub-xiphoid incision in the patent to compress the portion of the patient's tissue during a procedure.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIGS. 1 to 7 illustrate various views of an embodiment of a retractor member 10. Referring to the perspective view of the embodiment of a retractor member 10 illustrated in FIG. 1, the retractor member 10 may include a body portion 12 that may extend along a longitudinal axis 14 from a proximal end 16 to a distal end 18 that is opposite to the proximal end 16. The retractor member 10 may further include a first lateral support portion 32 coupled to the body portion 12 at a first location and a second lateral support portion 34 coupled to the body portion 12 at a second location. A first coupling portion 36 may be disposed at an end portion 38 of the first lateral support portion 32 and a second coupling portion 40 may be disposed at an end portion 42 of the second lateral support portion 34.

Figure 11:
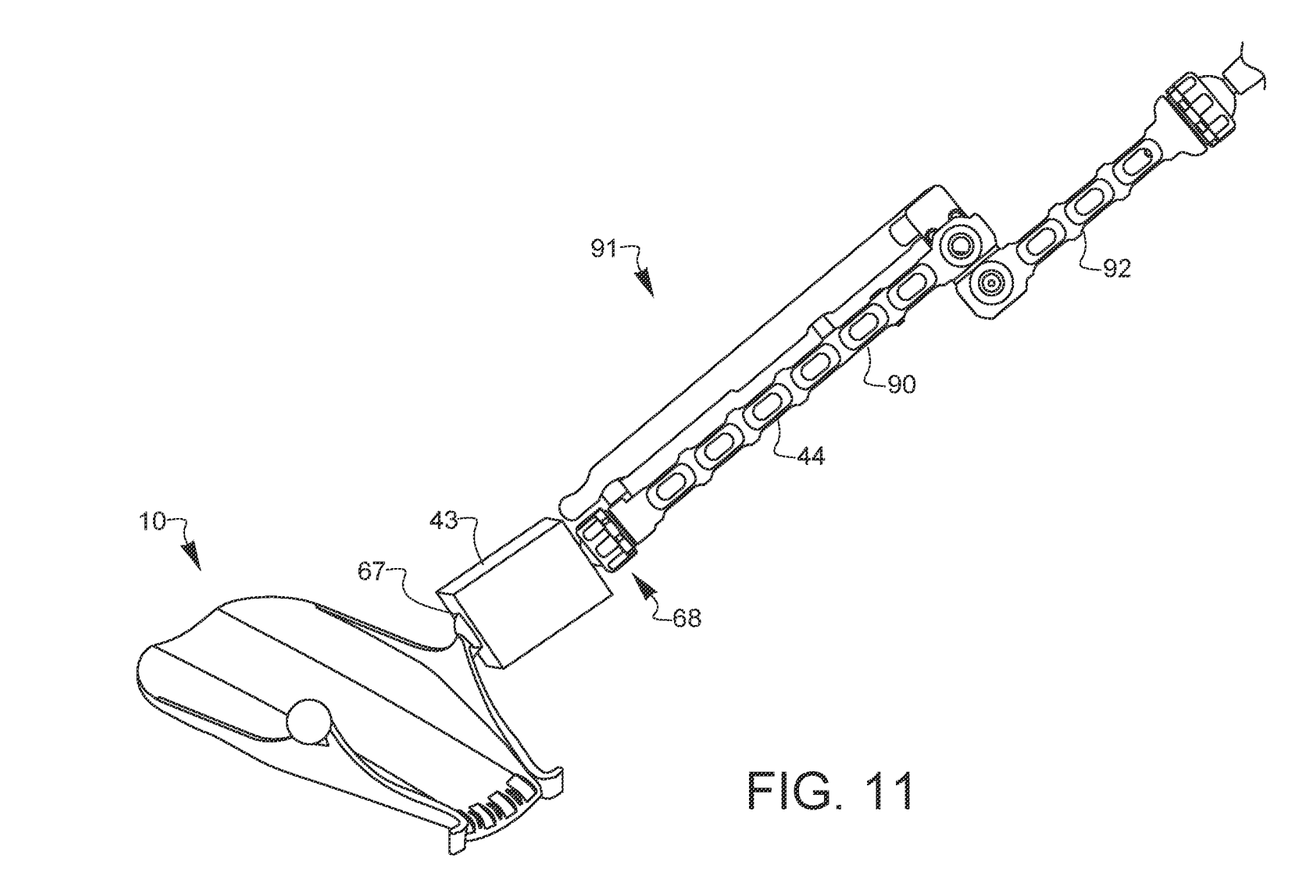
FIG. 11 is a perspective view of the embodiment of the retractor member of FIG. 1 having a second coupling portion coupled to a corresponding coupling portion of a surgical support instrument.
Figure 12:
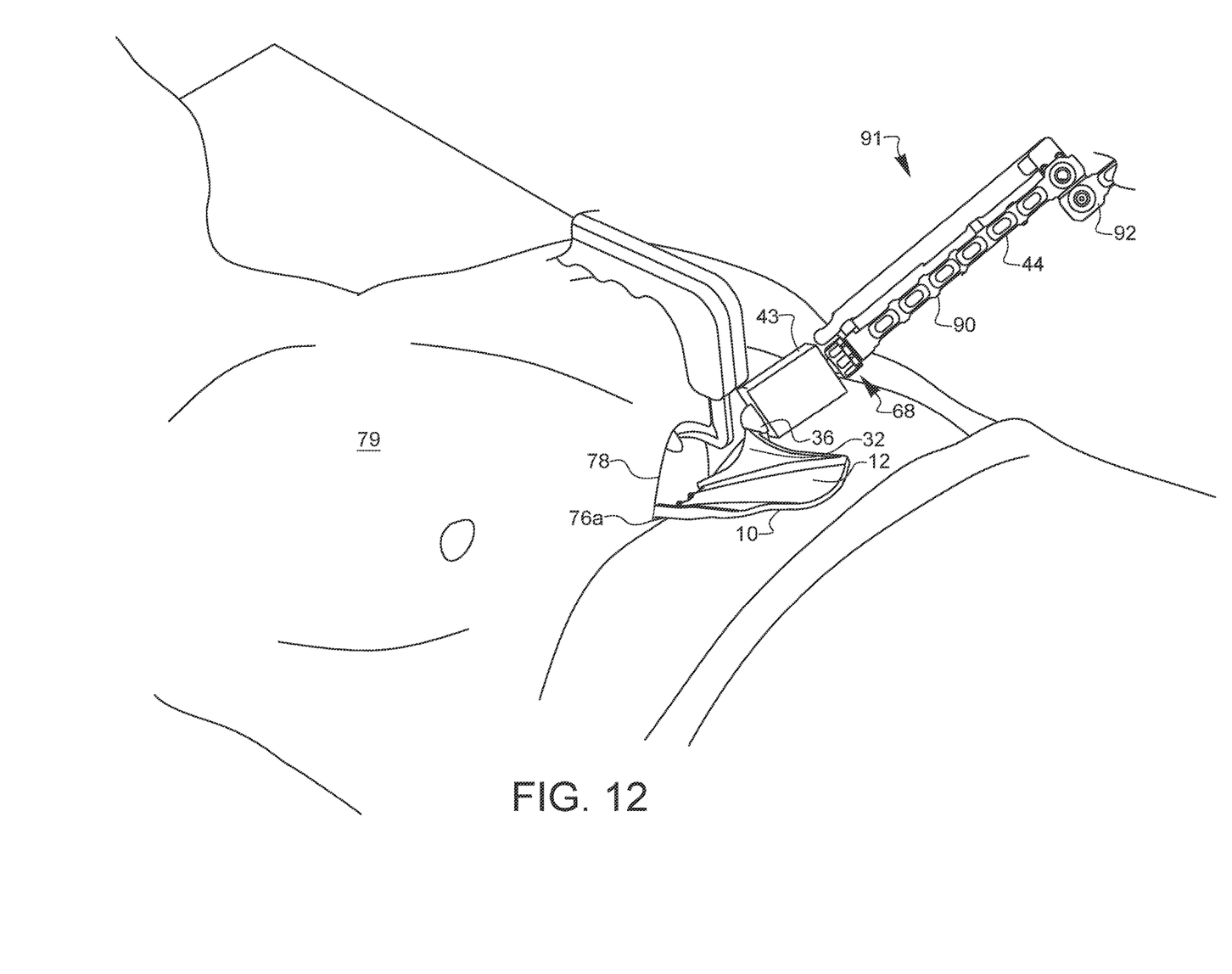
FIG. 12 is a perspective view of the embodiment of the retractor member of FIG. 11 with a distal end of the body portion disposed within a sub-xiphoid incision of a patient.

So configured, the first coupling portion 36 or the second coupling portion 40 may be adapted to be coupled to a corresponding coupling portion 43 of a surgical support instrument 44 (illustrated in FIG. 11) to stabilize the retractor member 10 when the distal end 18 of the body portion 12 is positioned in contact with a portion of a patient's 79 skin defining a sub-xiphoid incision 78, as illustrated in FIG. 12. The body portion 12 of the retractor member 10 may be positioned relative to the surgical support instrument 44 (and patient 79) by way of the first or second coupling portion's 36, 40 interaction with the coupling portion 43 of the surgical support instrument 44, and when the body portion 12 is positioned in a desired location, the first or second coupling portion 36, 40 may be locked or secured relative to the coupling portion 43 of the surgical support instrument 44 in a position in which a lower surface 45 of the body portion 12 (see FIG. 2) may contact one or more portions of the patient's epigastric region near the sub-xiphoid incision to compress one or more portions of the patient's epigastric region to create a larger access area surrounding the sub-xiphoid incision.

So positioned, the body portion 12 also provides a stable guide to support instruments (not shown) inserted by the surgeon into the sub-xiphoid incision, and one or more guide members 49 (see FIG. 6) may positioned at or adjacent to the distal end 18 of the body portion 12 to create dedicated regions along the body portion 12 for positioning and inserting the surgical instruments. The one or more guide members 49 may at least partially define longitudinal insertion channels for individual surgical tools that are to be used in a procedure, such as endoscopes, suturing tools, and the like.

Figure 1:
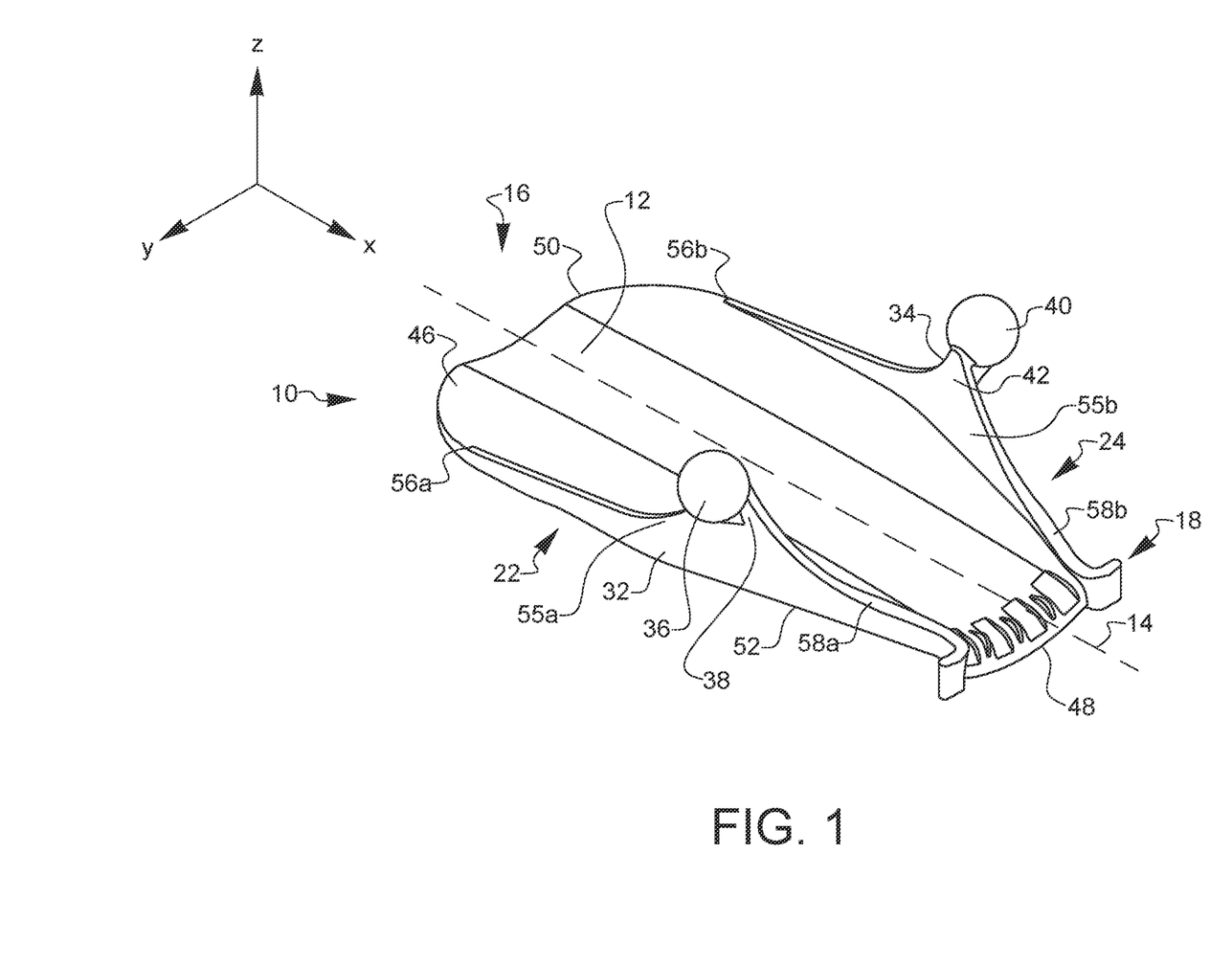
FIG. 1 is a perspective view of one embodiment of a retractor member.

Turning to the retractor member 10 in more detail, the body portion 12 may extend along or substantially along the longitudinal axis 14 from the proximal end 16 to the distal end 18, and the longitudinal axis 14 may be parallel to or aligned with the X-axis of the reference coordinate system provided in the perspective view of the retractor member 10 illustrated in FIG. 1. Referring to the front view of the retractor member 10 illustrated in FIG. 2, a transverse axis 20 may extend from a first lateral end 22 of the body portion 12 to a second lateral end 24 of the body portion 12 that is opposite to the first lateral end 22, and the transverse axis 20 may be normal to the longitudinal axis 14 and parallel to the Y-axis of the reference coordinate system provided in FIGS. 1 and 2. In addition, a vertical axis 26 may extend normal to both the transverse axis 20 and the longitudinal axis 14, and the vertical axis 26 may be parallel to the Z-axis of the reference coordinate system provided in FIGS. 1 and 2. Thus, a first vertical plane 28 may extend through the longitudinal axis 14 and the vertical axis 26 and may be parallel to or aligned with the X-Z-plane of the reference coordinate system provided in FIGS. 1 and 2. In some embodiments, the first vertical plane 28 may bisect the retractor member 10 and/or the body portion 12 into symmetrical or substantially symmetrical lateral half portions 30a, 30b. Further, as illustrated in the top view of the embodiment of the retractor member 10 illustrated in FIG. 6, a second vertical plane 29 may extend through the transverse axis 20 and the vertical axis 26 and may be parallel to the Y-Z-plane of the reference coordinate system provided in FIGS. 1 and 2.

Figure 6:
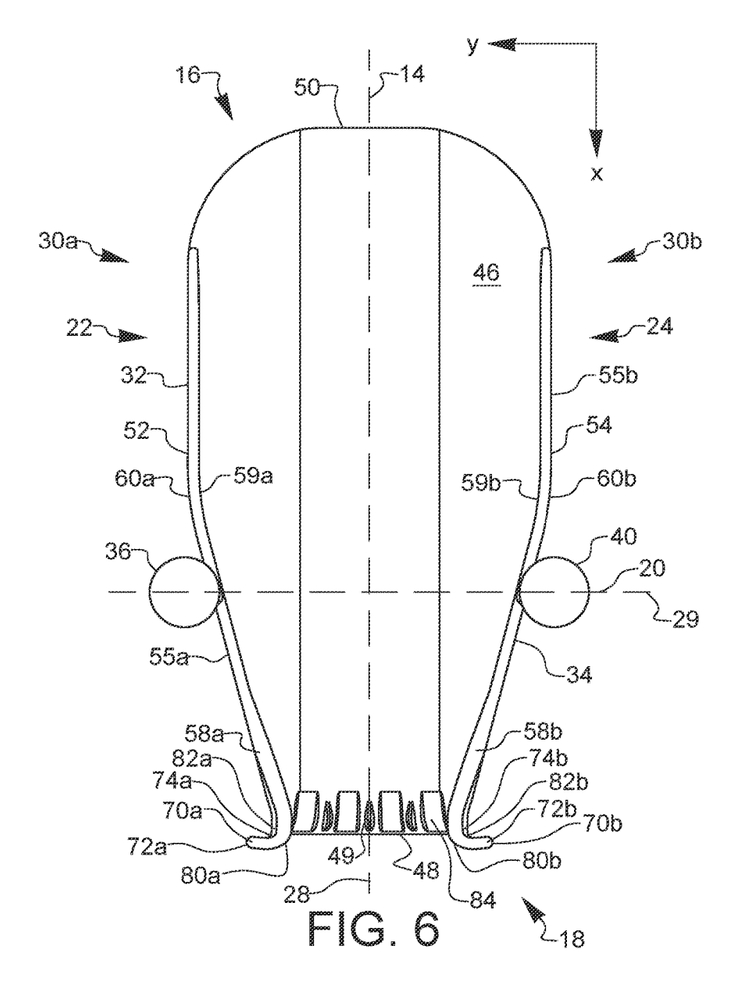
FIG. 6 is a top view of the embodiment of the retractor member illustrated in FIG. 1.
Figure 7:
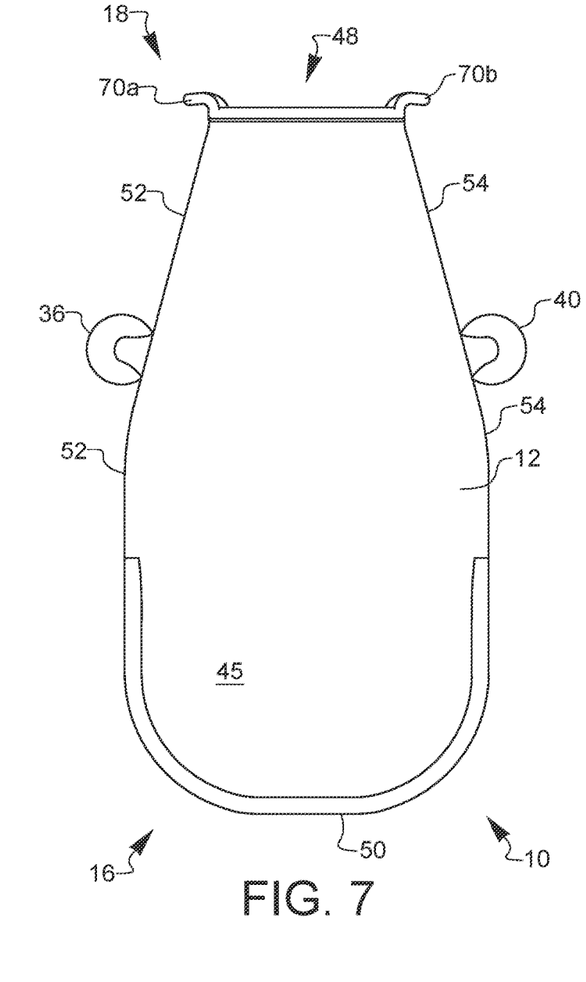
FIG. 7 is a bottom view of the embodiment of the retractor member illustrated in FIG. 1.
Figure 8:
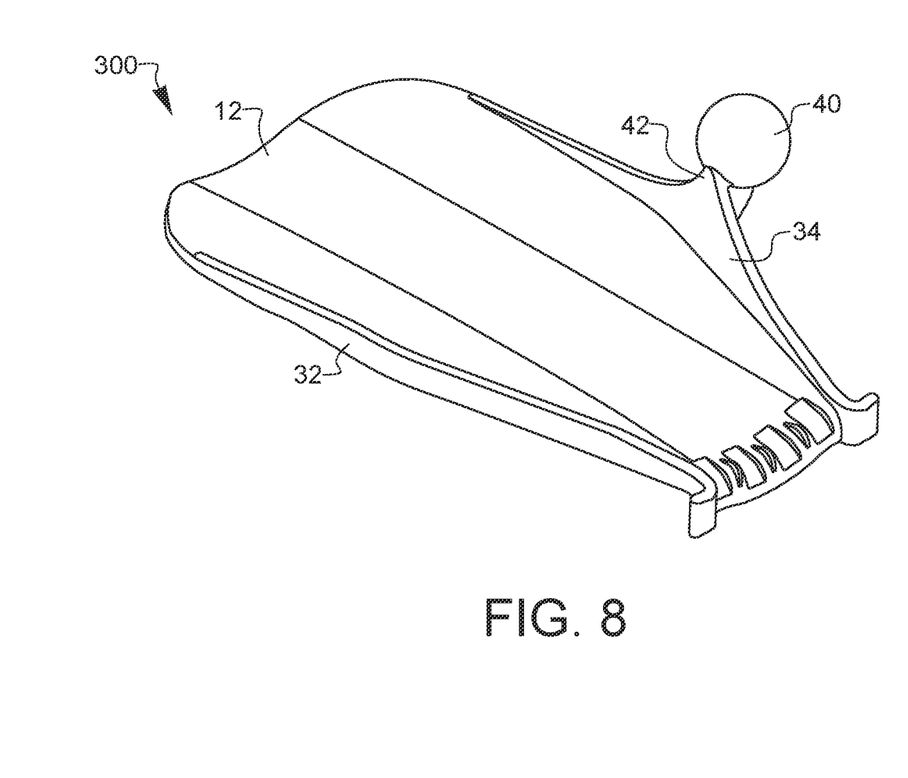
FIG. 8 is a perspective view of a second embodiment of a retractor member.

The body portion 12 may be defined by one or more perimeter edges. As illustrated in FIG. 6, the body portion 12 may be defined by a distal perimeter edge 48 disposed at the distal end 18 of the body portion 12, and the distal perimeter edge 48 may extend in a direction parallel or substantially parallel to the transverse axis 20. The distal perimeter edge 48 may extend in a direction that is linear or non-linear or a combination of linear and non-linear segments. The body portion 12 may also be defined by a proximal perimeter edge 50 disposed at the proximal end 16 of the body portion 12, and the proximal perimeter edge 50 may extend in a direc-tion parallel or substantially parallel to the transverse axis 20. The proximal perimeter edge 50 may extend in a direction that is linear or may be non-linear or a combination of linear and non-linear segments. For example, the proximal perimeter edge 50 may have a central linear segment surrounded by a radiused segment.

The body portion 12 may be further defined by a first lateral perimeter edge 52 that may extend from a first end portion of the distal perimeter edge 48 to a first end portion of the proximal perimeter edge 50, and the first lateral perimeter edge 52 may extend parallel or substantially parallel to the longitudinal axis 14, and may be offset from the longitudinal axis 14 in a first direction. In addition, the body portion 12 may be defined by a second lateral perimeter edge 54 that may extend from a second end portion of the distal perimeter edge 48 to a second end portion of the proximal perimeter edge 50, and the second lateral perimeter edge 54 may extend parallel or substantially parallel to the longitudinal axis 14 and may be offset from the longitudinal axis 14 in a second direction that is opposite to the first direction.

The body portion 12 may have any suitable shape to allow the lower surface 45 (illustrated in FIG. 7) to contact one or more portions of the patient's epigastric region near the sub-xiphoid incision to reposition one or more portions of the patient's epigastric region to create a larger access area surrounding the sub-xiphoid incision. For example, the body portion 12 may be thin-walled and contoured plate-like structure having a flat or substantially flat shape defined by an upper surface 46 (illustrated in FIG. 6) and the lower surface 45 (illustrated in FIG. 7). In other examples, the body portion 12 may have the shape of a plate-like structure having a contoured shape or a partially-contoured shape defined by the upper surface 46 and the lower surface 45. The distance between the upper surface 46 and the lower surface 45 (i.e., the thickness) of the body portion 12 may be constant or substantially constant, or may vary depending on the position along the body portion 12.

Figure 2:
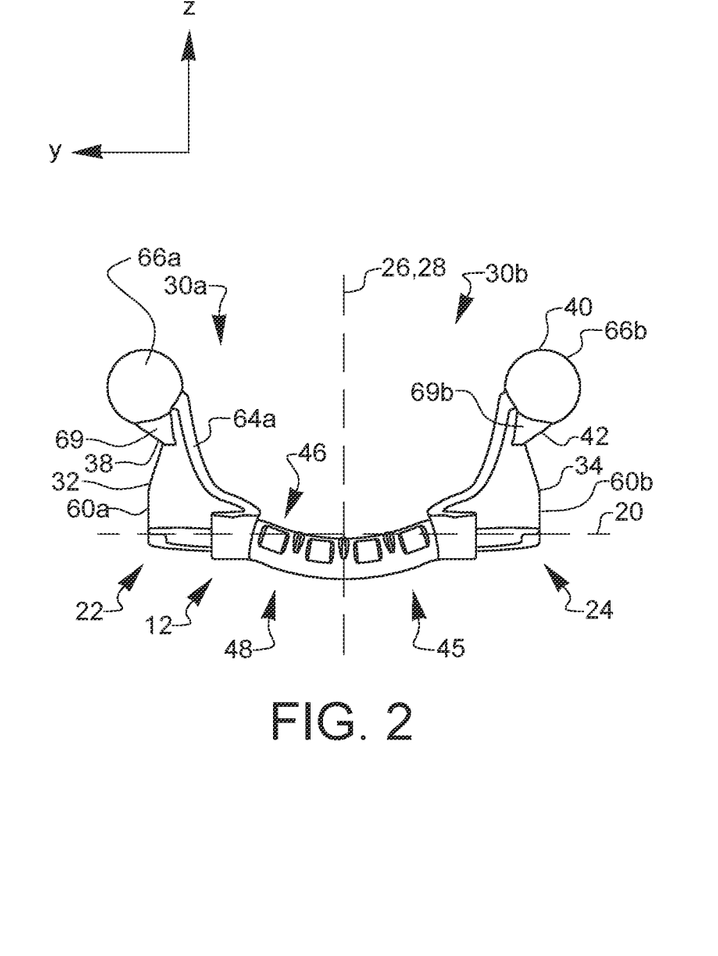
FIG. 2 is a front view of the embodiment of the retractor member illustrated in FIG. 1.
Figure 3:
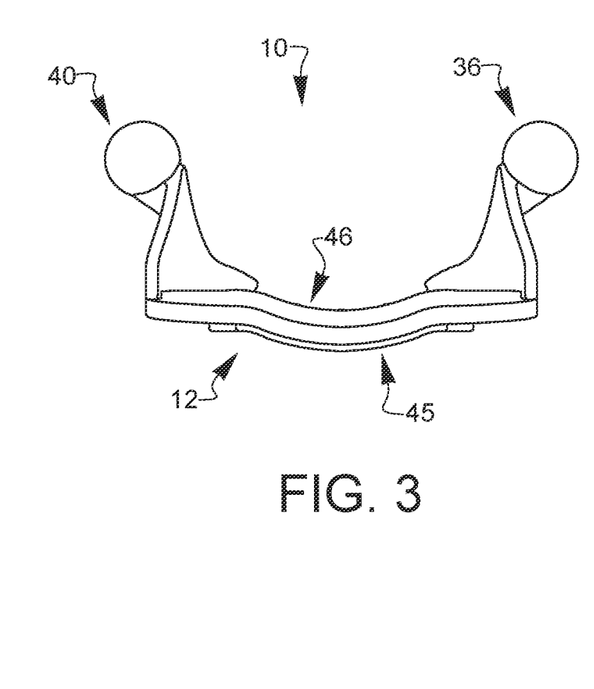
FIG. 3 is a rear view of the embodiment of the retractor member illustrated in FIG. 1.

For example, as illustrated in FIG. 2, all of a portion of the body portion 12 may have a cambered or slightly cambered shape when viewed along the longitudinal axis 14. That is, all or a portion of the upper surface 45 and lower surface 45 may each be concave or substantially concave along a cross-section taken along or in a plane parallel to the second vertical plane 29 illustrated in FIG. 6, wherein a middle portion of the upper surface 46 at or adjacent to the longitudinal axis 14 is lower (along the vertical axis 26) than the end portions that intersect each of the first lateral perimeter edge 52 and the second lateral perimeter edge 54.

Figure 4:
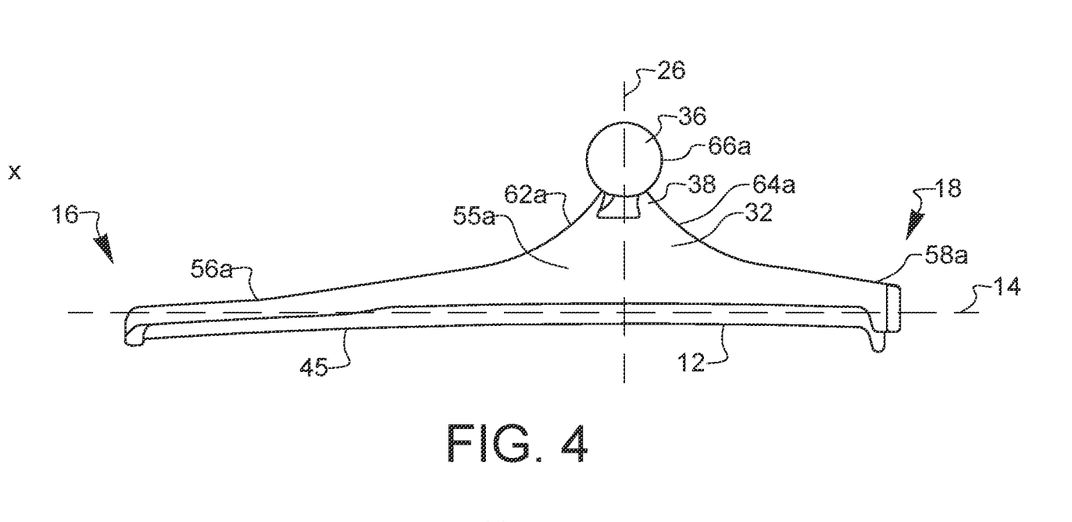
FIG. 4 is a first side view of the embodiment of the retractor member illustrated in FIG. 1.

In some embodiments, as illustrated in the side view of the embodiment of the retractor member 10 illustrated in FIG. 4, all or a portion of the body portion 12 may have a linear or substantially linear shape when viewed along the transverse axis 20. That is, all or a portion of the upper surface 45 and lower surface 46 may each be linear or substantially linear along a cross-section taken along or in a plane parallel to the first vertical plane 28 illustrated in FIG. 6.

Figure 10:
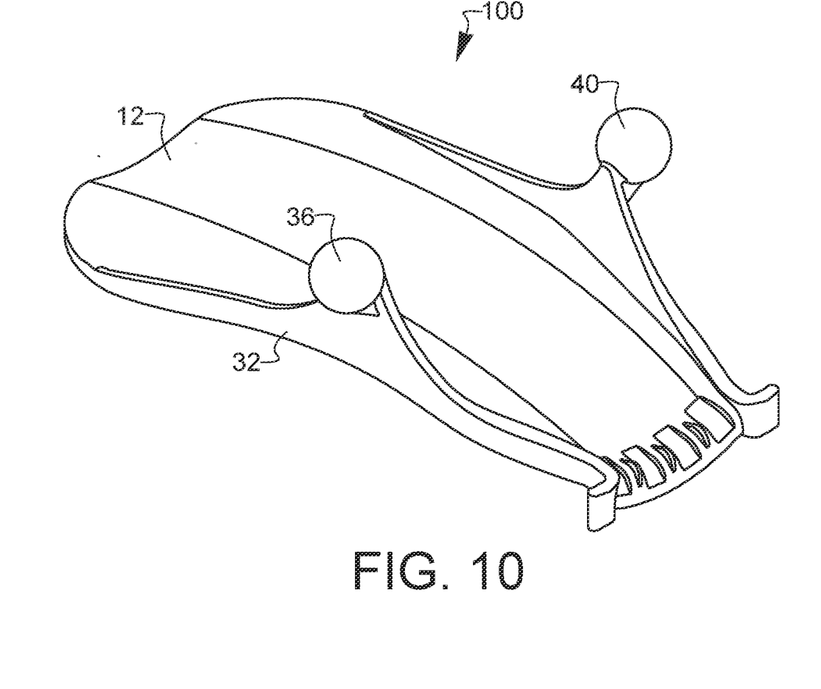
FIG. 10 is a perspective view of a fourth embodiment of a retractor member.

In other embodiments, such as the embodiment of a retractor member 100 illustrated in FIG. 10, all of a portion of the body portion 12 may have a cambered or slightly cambered shape when viewed along the transverse axis 20 (illustrated in FIG. 6). That is, all or a portion of the upper surface 45 and lower surface 46 may each be convex or substantially convex along a cross-section taken along or in a plane parallel to the first vertical plane 28 illustrated in FIG. 6, wherein a middle portion of the upper surface 45 at or adjacent to the longitudinal axis 14 is higher (along the vertical axis 26) than the end portions that intersect each of the distal perimeter edge 48 and the proximal perimeter edge 50. In this embodiment of the retractor member 100, the body portion 12 may have the general shape of a hyperbolic paraboloid. Such an embodiment facilitates the compression of the one or more portions of the patient's epigastric region by the lower surface 45 of the body portion 12 while allowing for a maximum access area into the sub-xiphoid incision.

In other embodiments, all or a portion of the upper surface 45 and lower surface 46 may each be concave or substantially concave along a cross-section taken along or in a plane parallel to the first vertical plane 28 illustrated in FIG. 6, wherein a middle portion of the upper surface 46 at or adjacent to the longitudinal axis 14 is lower (along the vertical axis 26) than the end portions that intersect each of the distal perimeter edge 48 and the proximal perimeter edge 50.

As previously discussed, the body portion 12 is configured to provide a stable guide or platform to support instruments (not shown) inserted by the surgeon into the sub-xiphoid incision. In particular, the body portion 12 may include the one or more guide members 49 (see FIG. 6, which illustrates a first guide member, a second guide member, and a third guide member) positioned at or adjacent to the distal end 18 of the body portion 12 to create dedicated regions along the body portion 12 for positioning and inserting the surgical instruments, and the one or more guide members 49 may define or at least partially define longitudinal insertion channels for individual elongated surgical tools that are to be used in a procedure, such as endoscopes, suturing tools, and the like. Each or any of the one or more guide members 49 may be a protrusion, a rib, or a wall extending vertically from the upper surface 46 of the body portion 12. The protrusion, rib, or wall may be elongated and may extend from a proximal end to a distal end along an axis that is parallel to or aligned with the longitudinal axis 14. Any number of additional guide members 49 may be disposed on the body portion 12 proximal to the distal end 18 of the body portion 12 to define or at least partially define the longitudinal insertion channels. One or more depressions 84 may be disposed in each of the longitudinal insertion channels between adjacent guide members 49 to assist in maintaining alignment of surgical tools.

Referring to FIG. 1, the retractor member 10 may include the first lateral support portion 32 coupled to the body portion 12 at a first location that is disposed along or adjacent to the first lateral perimeter edge 52. In particular, the first lateral support portion 32 may be an elongated side wall 55a that may extend from a proximal end 56a to a distal end 58a, and the side wall 55a may be partially-defined by an interior surface 59a and an oppositely-disposed exterior surface 60a, as illustrated in FIG. 6. The distance between the interior surface 59a and the exterior surface 60a (i.e., the thickness) of the side wall 55a may be constant or substantially constant such that the side wall 55a may have a plate-like structure that extends in a direction along or generally along the vertical axis 26 from the first lateral perimeter edge 52. As illustrated in FIG. 6, the side wall 55a may be contoured to extend along all or a portion of the first lateral perimeter edge 52 from the proximal end 56a to the distal end 58a. That is, the proximal end 56a may be disposed distal to the proximal end 16 of the body portion 12, and the distal end 58a may be disposed proximal to the distal end 18 of the body portion 12. However, the proximal end 56a may be disposed at or adjacent to the proximal end 16 of the body portion 12, and the distal end 58a may be at or adjacent to the distal end 18 of the body portion 12. When viewed along the transverse axis 20, as illustrated in FIG. 4, the side wall 55a may have a triangular or generally triangular shape, and a first perimeter edge 62a and a second perimeter edge 64a defining the side wall 55a may each extend obliquely towards the vertical axis 26 such that the end portion 38 of the first lateral support portion 32 is at or adjacent to the apex of the triangular side wall 55a.

In other embodiments, the first lateral support portion 32 may have any suitable shapes or combination of shapes that provide support to the first coupling portion 36 and allow the first coupling portion 36 to be vertically offset from the body portion 12.

Referring to FIG. 6, the retractor member 10 may include a first distal lip 70a that may be disposed at or adjacent to the distal end 18 of the body portion 12. The first distal lip 70a may extend from the distal end 58a of the first lateral support portion 32 and may have a surface that is coextensive with the exterior surface 60a of the side wall 55a of the first lateral support portion 32. In other embodiments, the first distal lip 70a may not extend from, and may be longitudinally spaced from, the distal end 58a of the first lateral support portion 32.

The first distal lip 70a may have a curved shape when viewed along the vertical axis 26, and an end portion 72a of the first distal lip 70a may extend transversely (i.e., along or substantially along the transverse axis 20) to allow an outer surface 82a to at least partially define a rounded shoulder portion 74a. As illustrated in FIG. 12, the shoulder portion 74a may be configured to capture a first edge portion 76a of an incision 78 in a patient 79 to secure the retractor member 10 relative to and/or within the incision 78. The end portion 72a of the first distal lip 70a may have any suitable shape to capture the first edge portion 76a of the incision 78 while avoiding trauma to the patient. For example, the end portion 72a may have a rectangular or generally rectangular cross-sectional shape along a plane parallel to the first vertical place 28 when viewed along the transverse axis 20. The corners and/or edges of the end portion 72a may be radiused or rounded. An interior surface 80a that partially defines the shoulder portion 74a may be configured to provide a barrier to prevent surgical instruments disposed along the body portion 12 from falling off of the body portion 12 and/or to remain aligned along the body portion 12.

With reference to FIG. 6, the retractor member 10 may include a second distal lip 70b that may have any suitable shape or combination of shapes. In some embodiments, the second distal lip 70b may be a mirror-image of, but otherwise identical to, the first distal lip 70a previously described. That is, the second distal lip 70b may be disposed at or adjacent to the distal end 18 of the body portion 12. The second distal lip 70b may extend from the distal end 58b of the second lateral support portion 34 and may have a surface that is coextensive with the exterior surface 60b of the side wall 55b of the second lateral support portion 34. In other embodiments, the second distal lip 70b may not extend from, and may be longitudinally spaced from, the distal end 58b of the second lateral support portion 34.

The second distal lip 70b may have a curved shape when viewed along the vertical axis 26, and an end portion 72b of the second distal lip 70b may extend transversely (i.e., along or substantially along the transverse axis 20) to allow an outer surface 82b to at least partially define a rounded shoulder portion 74b. As illustrated in FIG. 12, the shoulder portion 74b is configured to capture a second edge portion (not visible) of the incision 78 in the patient 79 to secure the retractor member 10 relative to and/or within the incision 78. The end portion 72b of the second distal lip 70b may have any suitable shape to capture the second edge portion of the incision 78 while avoiding trauma to the patient. For example, the end portion 72b may have a rectangular or generally rectangular cross-sectional shape along a plane parallel to the first vertical place 28 when viewed along the transverse axis 20. The corners and/or edges of the end portion 72b may be radiused or rounded. An interior surface 80b that partially defines the shoulder portion 74b may be configured to provide a barrier to prevent surgical instruments disposed along the body portion 12 from falling off of the body portion 12 and/or to remain aligned along the body portion 12.

Referring to FIGS. 1, 2, and 4, the retractor member 10 may include the first coupling portion 36. In some embodiments, the first coupling portion 36 may be disposed at the end portion 38 of the first lateral support portion 32. In other embodiments, the first coupling portion 36 may be disposed at any portion or portions of the first lateral support portion 32. The first coupling portion 36 may be any feature or combination of features that are configured to be coupled to the corresponding coupling portion 43 of a surgical support instrument 44 (illustrated in FIG. 11).

As illustrated in FIG. 2, the first coupling portion 36 may be a ball 66a that may comprise a full or partial sphere. The ball 66a may be disposed at or adjacent to the apex of the triangular side wall 55a, and one or more supporting members, such as a rib 69a, may extend between one or more portions of the ball 66a and one or more portions of the side wall 55a. The ball 66a may be configured to be accepted into a corresponding socket portion 67 that comprises all or a portion of the coupling portion 43 of the surgical support instrument 44. In some embodiments, the socket portion 67 may removably accept the ball 66a such that the retractor member 10 may be removably coupled to the coupling portion 43 of a surgical support instrument 44. In other embodiments, the socket portion 67 may be non-removably coupled to the ball 66a, and all or a portion of the coupling portion 43 of a surgical support instrument 44 may be removably coupled to a distal end 68 of the surgical instrument 44. With the ball 66a received in the socket portion 67, the body member 12 (and/or the retractor member 10) may freely rotate in two planes at the same time while preventing translation relative to the distal end of the surgical support instrument 44. Thus, the body portion 12 of the retractor member 10 may be positionable relative to the distal end 68 of the surgical instrument 44 to achieve a desired position relative to the patient's incision.

The first coupling portion 36 may also be selectively lockable relative to the corresponding coupling portion 43 of a surgical support instrument 44. For example, the ball 66a may be configured to be accepted into a corresponding socket portion 67 such that in an unlocked socket position, the ball 66a may rotate freely within the socket portion 67 and in a locked socket position, the ball 66a may be locked within the socket portion 67. A user may displace the socket portion 67 between the unlocked socket position and the locked socket position in any suitable manner, such as by pinching a portion of the socket portion 67 to displace the socket portion 67 from the locked socket position to the unlocked socket position, and the portion of the socket portion 67 may be released by the user to displace the socket portion 67 from the unlocked socket position to the locked socket position. In some embodiments, in the locked socket position, the ball 66a may frictionally engage the socket portion 67 such that the ball 66a may displace within the socket portion 67 when subjected to a relatively large degree of force by a user, but the ball 66a may not displace within the socket portion 67 when subjected to a relatively small degree of force. In some embodiment, the ball 66a may always be in a locked socket position such that the ball 66a may displace within the socket portion 67 when subjected to a relatively large degree of force by a user, but the ball 66a may not displace within the socket portion 67 when subjected to a relatively small degree of force.

Referring again to FIG. 1, the retractor member 10 may include the second lateral support portion 34 coupled to the body portion 12 at a second location that is disposed along or adjacent to the second lateral perimeter edge 54. The second lateral support portion 34 may have any suitable shape or combination of shapes. In some embodiments, the second lateral support portion 34 may be a mirror-image of, but otherwise identical to, the first lateral support portion 32 previously described.

In particular, the second lateral support portion 34 may be an elongated side wall 55b that may extend from a proximal end 56b to a distal end 58b, and the side wall 55b may be partially-defined by an interior surface 59b and an oppositely-disposed exterior surface 60b, as illustrated in FIG. 6. The distance between the interior surface 59b and the exterior surface 60b (i.e., the thickness) of the side wall 55b may be constant or substantially constant such that the side wall 55b may have a plate-like structure that extends in a direction along or generally along the vertical axis 26 from the second lateral perimeter edge 54. As illustrated in FIG. 6, the side wall 55b may be contoured to extend along all or a portion of the second lateral perimeter edge 54 from the proximal end 56b to the distal end 58b. That is, the proximal end 56b may be disposed distal to the proximal end 16 of the body portion 12, and the distal end 58b may be disposed proximal to the distal end 18 of the body portion 12. However, the proximal end 56b may be disposed at or adjacent to the proximal end 16 of the body portion 12, and the distal end 58b may be at or adjacent to the distal end 18 of the body portion 12. When viewed along the transverse axis 20, as illustrated in FIG. 5, the side wall 55b may have a triangular or generally triangular shape, and a first perimeter edge 62b and a second perimeter edge 64b defining the side wall 55b may each extend obliquely towards the vertical axis 26 such that the end portion 42 of the second lateral support portion 34 is at or adjacent to the apex of the triangular side wall 55b.

In other embodiments, the second lateral support portion 34 may have any suitable shapes or combination of shapes that provide support to the first coupling portion 36 and allow the first coupling portion 36 to be vertically offset from the body portion 12, and the second lateral support portion 34 may generally correspond in shape to the first lateral support portion 32.

Figure 5:
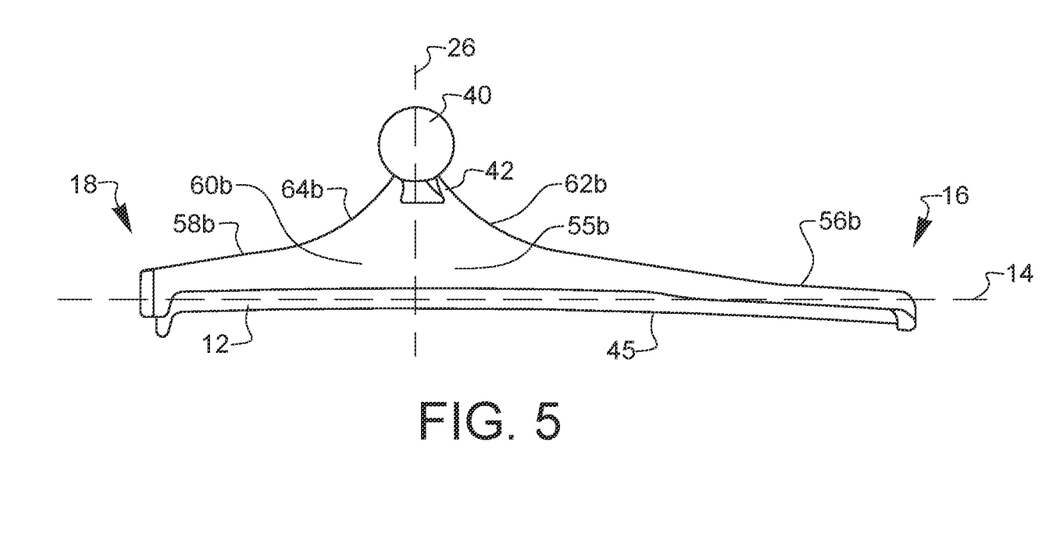
FIG. 5 is a second side view of the embodiment of the retractor member illustrated in FIG. 1.

Referring to FIGS. 1, 2, and 5, the retractor member 10 may include the second coupling portion 40, which may be a mirror-image of, but otherwise identical to, the first coupling portion 36 previously described. In some embodiments, the second coupling portion 40 may be disposed at the end portion 42 of the second lateral support portion 34. In other embodiments, the second coupling portion 40 may be disposed at any portion or portions of the second lateral support portion 34. The second coupling portion 40 may be any feature or combination of features that are configured to be coupled to the corresponding coupling portion 43 of a surgical support instrument 44 (illustrated in FIG. 11). As illustrated in FIG. 2, the second coupling portion 40 may be a ball 66b that may comprise a full or partial sphere and may be identical in shape in function to the ball 66a of the first coupling portion 36 previously described. That is, the ball 66b may be disposed at or adjacent to the apex of the triangular side wall 55b, and one or more supporting members, such as a rib 69b, may extend between one or more portions of the ball 66b and one or more portions of the side wall 55b. The ball 66b may be configured to be accepted into a corresponding socket portion 67 that comprises all or a portion of the coupling portion 43 of the surgical support instrument 44. In some embodiments, the socket portion 67 may removably accept the ball 66b such that the retractor member 10 may be removably coupled to the coupling portion 43 of the surgical support instrument 44. In other embodiments, the socket portion 67 may be non-removably coupled to the ball 66b, and all or a portion of the coupling portion 43 of a surgical support instrument 44 may be removably coupled to a distal end 68 of the surgical instrument 44.

The second coupling portion 40 may also be selectively lockable relative to the corresponding coupling portion 43 of a surgical support instrument 44. For example, the ball 66b may be configured to be accepted into a corresponding socket portion 67 such that in an unlocked socket position, the ball 66b may rotate freely within the socket portion 67 and in a locked socket position, the ball 66b may be locked within the socket portion 67. A user may displace the socket portion 67 between the unlocked socket position and the locked socket position in any suitable manner, such as by pinching a portion of the socket portion 67 to displace the socket portion 67 from the locked socket position to the unlocked socket position, and the portion of the socket portion 67 may be released by the user to displace the socket portion 67 from the unlocked socket position to the locked socket position. In some embodiments, in the locked socket position, the ball 66b may frictionally engage the socket portion 67 such that the ball 66b may displace within the socket portion 67 when subjected to a relatively large degree of force by a user, but the ball 66b may not displace within the socket portion 67 when subjected to a relatively small degree of force. In some embodiment, the ball 66b may always be in a locked socket position such that the ball 66b may displace within the socket portion 67 when subjected to a relatively large degree of force by a user, but the ball 66b may not displace within the socket portion 67 when subjected to a relatively small degree of force.

Figure 9:
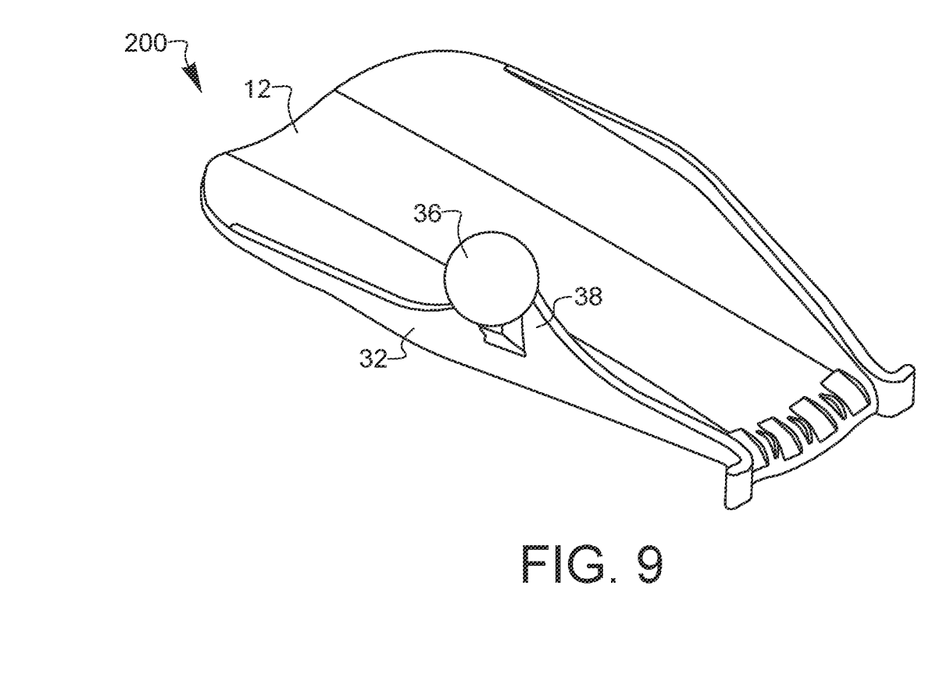
FIG. 9 is a perspective view of a third embodiment of a retractor member.

As illustrated in the perspective view of an embodiment of the retractor member 200 illustrated in FIG. 9, the retractor member 200 may include the first lateral support portion 32 coupled to the body portion 12 at the first location and the first coupling portion 36 disposed at the end portion 38 of the first lateral support portion 32. However, the retractor member 200 may not have the second coupling portion 40 disposed at an end portion 42 of the second lateral support portion 34. In this embodiment, the second lateral support portion 34 may have a different shape than the first lateral support portion 32. In some embodiments, not shown, the retractor member 200 may not have the second lateral support portion 34 and the second coupling portion 40. This configuration allows for a surgeon to access an area of the body portion 12 that may have been blocked or obstructed by the second coupling portion 40.

Similarly, and as illustrated in the perspective view of an embodiment of the retractor member 300 illustrated in FIG. 6, the retractor member 300 may include the second lateral support portion 34 coupled to the body portion 12 at a second location and the second coupling portion 40 disposed at the end portion 42 of the second lateral support portion 34. However, the retractor member 300 may not have a first coupling portion 36 disposed at an end portion 38 of the first lateral support portion 32. In this embodiment, the first lateral support portion 32 may have a different shape than the second lateral support portion 34. In some embodiments, not shown, the retractor member 300 may not have the first lateral support portion 32 and the first coupling portion 36. This configuration allows for a surgeon to access an area of the body portion 12 that may have been blocked or obstructed by the first coupling portion 36.

In some embodiment, all or a part of the retractor member 10, 100, 200, 300 may be integrally formed. That is, in some embodiments, the retractor member 10, 100, 200, 300 may be formed, manufactured, or fabricated as a single, unitary part from a single piece of material. In some embodiments, the retractor member 10, 100, 200, 300 may be a plastic part (e.g., polypropylene) that is injection molded as a single, unitary part. However, the retractor member 10, 100, 200, 300 may be made of any suitable material, such as a metal material or a thermoplastic material.

In some embodiments, a soft or flexible layer of plastic material, such as an elastomer or silicone, may cover all or a portion of the material of the retractor member 10, 100, 200, 300 to reduce trauma to the soft tissue of the patient in contact with the retractor member 10, 100, 200, 300. For example, all or a portion of the first distal lip 70a and/or the second distal lip 70b, and/or the lower surface 46 of the body portion 12 may be coated or covered with a soft layer.

While the retractor member 10, 100, 200, 300 was disclosed as being used in an ITA harvesting and CABG procedure, the retractor member 10, 100, 200, 300 may be used in other surgical procedures involving a sub-xiphoid incision, such as epicardial lead placement, or any other type of incision.

The surgical support instrument 44 may be any suitable instrument that is capable of coupling to providing support for the retractor member 10, 100, 200, 300 during a procedure, and the surgical support instrument 44 and the retractor member 10, 100, 200, 300 may comprise a surgical device assembly 91. For example, in the embodiment illustrated in FIGS. 11 and 12, the surgical support instrument 44 of the surgical device assembly 91 may include an elongated first arm 90 having a proximal end and a distal end, and an elongated second arm 92 having a proximal end and a distal end. The distal end of the second arm 92 may be rotatably, pivotably, or otherwise displaceably coupled to the proximal end of the first arm 90 (by, for example, a ball joint) such that the first arm 90 is pivotable relative to the second arm 92. The distal end of the second arm 92 may be selectively lockable relative to the proximal end of the first arm 90 such that the first arm 90 is pivotable relative to the second arm 92 in a first unlocked position and such that the first arm 90 is not pivotable relative to the second arm 92 in a second locked position. The proximal end of the second arm 92 may be directly or indirectly coupled to a stabilizing portion (e.g., a portion of a stable rail) such that the first arm 90 and second arm provide a rigid and stable base of support when the first arm 90 and the second arm 92 are in the second locked position. The coupling portion 43 of the surgical support instrument 44 may be disposed at or coupled to the distal end of the first arm 90, and as previously explained, the coupling portion 43 may include the socket portion 67. In some embodiments, the surgical support instrument 44 may be disclosed in U.S. patent application Ser. No. 16/610,311, entitled "SURGICAL EQUIPMENT HOLDER and filed on Nov. 1, 2019, the contents of which is incorporated by reference in its entirety. The surgical support instrument 44 may be a part of a miniARM™ System available from LSI SOLUTIONS® (www.lsisolutions.com) located in Victor, N.Y.

Various advantages of a surgical retractor member have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A retractor member comprising:
    a body portion extending along a longitudinal axis from a proximal end to a distal end, the body portion being at least partially defined by:
        a first lateral perimeter edge that extends generally parallel to the longitudinal axis;
        a second lateral perimeter edge that extends generally parallel to the longitudinal axis;
        an upper surface that extends between the first lateral perimeter edge and the second lateral perimeter edge; and
        a lower surface that extends between the first lateral perimeter edge and the second lateral perimeter edge;
    a first lateral support portion coupled to the body portion at a first location at or adjacent to the first lateral perimeter edge;
    a second lateral support portion coupled to the body portion at a second location at or adjacent to the second lateral perimeter edge;
    a first coupling portion disposed at a top end portion of the first lateral support portion; and
    a second coupling portion disposed at a top end portion of the second lateral support portion,
    wherein one of the first coupling portion or the second coupling portion is configured to be removably and rotatably secured to a coupling portion disposed at a distal end of a surgical support instrument that is adapted to stabilize and support the retractor member, and wherein the retractor member is configured to be selectively repositionable relative to the coupling portion at the distal end of the surgical support instrument such that the lower surface of the body portion is configured to be disposed in contact with a portion of a patient's tissue that is adjacent to a sub-xiphoid incision in the patent to compress the portion of the patient's tissue during a procedure.

2. The retractor member of claim 1, wherein the first coupling portion is a spherical ball member or partially spherical ball member that is configured to be received into a corresponding socket portion disposed on the coupling portion at the distal end of the surgical support instrument.

3. The retractor member of claim 1, wherein the body portion is at least partially defined by a distal perimeter edge that extends between a distal end of the first lateral perimeter edge and a distal end of the second lateral perimeter edge, and wherein the distal perimeter edge is linear.

4. The retractor member of claim 1, wherein the body portion is a plate-like structure such that a first cross-sectional shape of the upper surface and the lower surface is linear when viewed along a transverse axis that is normal to the longitudinal axis.

5. The retractor member of claim 4, wherein a second cross-sectional shape of the upper surface and the lower surface is linear when viewed along the longitudinal axis.

6. The retractor member of claim 4, wherein a second cross-sectional shape of the upper surface and the lower surface is cambered when viewed along the longitudinal axis.

7. The retractor member of claim 1, wherein the body portion has a contoured shape such that a first cross-sectional shape of the upper surface and the lower surface is cambered when viewed along a transverse axis that is normal to the longitudinal axis.

8. The retractor member of claim 7, wherein a second cross-sectional shape of the upper surface and the lower surface is cambered when viewed along the longitudinal axis.

9. The retractor member of claim 1, further comprising a first guide member, a second guide member, and a third guide member disposed on the upper surface of the body portion at or adjacent to the distal end of the body portion, each of the first guide member, the second guide member, and the third guide member being an elongated protrusion having a long axis that is parallel to the longitudinal axis of the body portion, the first guide member, the second guide member, and the third guide member cooperating to define longitudinal insertion channels configured to allow for defined placement of one or more individual surgical tools that are to be used in the procedure.

10. The retractor member of claim 1, wherein the first lateral support portion is an elongated side wall that extends along the first lateral perimeter edge from a proximal end that is distal to a proximal end of the first lateral perimeter edge to a distal end that is proximal a distal end of the first lateral perimeter edge, and wherein the second lateral support portion is an elongated side wall that extends along the second lateral perimeter edge from a proximal end that is distal to a proximal end of the second lateral perimeter edge to a distal end that is proximal to a distal end of the second lateral perimeter edge.

11. The retractor member of claim 10, wherein the first lateral support portion has a generally triangular shape when viewed along a transverse axis that is normal to the longitudinal axis, and wherein the second lateral support portion has a generally triangular shape when viewed along the transverse axis.

12. A surgical device assembly comprising:
    a retractor member comprising:
        a body portion extending along a longitudinal axis from a proximal end to a distal end, the body portion being at least partially defined by:
            a first lateral perimeter edge that extends generally parallel to the longitudinal axis;
            a second lateral perimeter edge that extends generally parallel to the longitudinal axis;
            an upper surface that extends between the first lateral perimeter edge and the second lateral perimeter edge; and
            a lower surface that extends between the first lateral perimeter edge and the second lateral perimeter edge;

a first lateral support portion coupled to the body portion at a first location at or adjacent to the first lateral perimeter edge;

a second lateral support portion coupled to the body portion at a second location at or adjacent to the second lateral perimeter edge;

a first coupling portion disposed at a top end portion of the first lateral support portion; and a second coupling portion disposed at a top end portion of the second lateral support portion; and a surgical support instrument comprising:

an elongated first arm having a proximal end and a distal end;

an elongated second arm having a proximal end and a distal end, the distal end of the second arm being rotatably coupled to the proximal end of the first arm, and the proximal end of the second arm being coupled to a stabilizing portion such that the first arm and second arm provide a rigid support; and a coupling portion disposed at the distal end of the first arm, wherein one of the first coupling portion or the second coupling portion of the retractor member is removably and rotatably secured to the coupling portion, and wherein the retractor member is configured to be selectively repositionable relative to the coupling portion such that the lower surface of the body portion of the retractor member is configured to be disposed in contact with a portion of a patient's tissue that is adjacent to a sub-xiphoid incision in the patent to compress the portion of the patient's tissue during a procedure.

13. The surgical device assembly of claim 12, wherein the first coupling portion is a spherical ball member or partially spherical ball member that is configured to be received into a corresponding socket portion disposed on the coupling portion at the distal end of the surgical support instrument.

14. The surgical device assembly of claim 12, wherein the body portion is a plate-like structure such that a first cross-sectional shape of the upper surface and the lower surface is linear when viewed along a transverse axis that is normal to the longitudinal axis.

15. The surgical device assembly of claim 14, wherein a second cross-sectional shape of the upper surface and the lower surface is linear when viewed along the longitudinal axis.

16. The surgical device assembly of claim 14, wherein a second cross-sectional shape of the upper surface and the lower surface is cambered when viewed along the longitudinal axis.

17. The surgical device assembly of claim 12, wherein the body portion has a contoured shape such that a first cross-sectional shape of the upper surface and the lower surface is cambered when viewed along a transverse axis that is normal to the longitudinal axis.

18. The surgical device assembly of claim 17, wherein a second cross-sectional shape of the upper surface and the lower surface is cambered when viewed along the longitudinal axis.

19. The surgical device assembly of claim 12, wherein the first lateral support portion is an elongated side wall that extends along the first lateral perimeter edge from a proximal end that is distal to a proximal end of the first lateral perimeter edge to a distal end that is proximal a distal end of the first lateral perimeter edge, and wherein the second lateral support portion is an elongated side wall that extends along the second lateral perimeter edge from a proximal end that is distal to a proximal end of the second lateral perimeter edge to a distal end that is proximal to a distal end of the second lateral perimeter edge.

20. The surgical device assembly of claim 19, wherein the first lateral support portion has a generally triangular shape when viewed along a transverse axis that is normal to the longitudinal axis, and wherein the second lateral support portion has a generally triangular shape when viewed along the transverse axis.

* * * * *